(12) United States Patent
Neuhaus et al.

(10) Patent No.: US 11,497,868 B2
(45) Date of Patent: Nov. 15, 2022

(54) DISPLAY FOR OUTPUTTING INFORMATION CONTENTS OF MEDICAL DEVICES

(71) Applicant: WEINMANN EMERGENCY MEDICAL TECHNOLOGY GMBH + CO. KG, Hamburg (DE)

(72) Inventors: Christian Neuhaus, Hamburg (DE); Norman Scotti, Sylt OT Tinnum (DE); Milos Dordevic, Hamburg (DE)

(73) Assignee: WEINMANN EMERGENCY MEDICAL TECHNOLOGY GMBH + CO. KG, Hamburg (DE)

( * ) Notice: Subject to any disclaimer, the term of this patent is extended or adjusted under 35 U.S.C. 154(b) by 559 days.

(21) Appl. No.: 16/605,368

(22) PCT Filed: Feb. 16, 2018

(86) PCT No.: PCT/DE2018/000040
§ 371 (c)(1),
(2) Date: Oct. 15, 2019

(87) PCT Pub. No.: WO2018/196894
PCT Pub. Date: Nov. 1, 2018

(65) Prior Publication Data
US 2021/0121650 A1 Apr. 29, 2021

(30) Foreign Application Priority Data

Apr. 27, 2017 (DE) ..................... 10 2017 004 140.7
Aug. 9, 2017 (DE) ..................... 10 2017 007 625.1

(51) Int. Cl.
*A61M 16/00* (2006.01)
*A61N 1/39* (2006.01)
(Continued)

(52) U.S. Cl.
CPC ....... *A61M 16/0051* (2013.01); *A61N 1/3993* (2013.01); *G06T 11/001* (2013.01);
(Continued)

(58) Field of Classification Search
CPC ..... A61B 5/742; A61B 5/7435; A61B 5/7445; A61B 5/743; A61B 5/7425; A61B 5/7475;
(Continued)

(56) References Cited

U.S. PATENT DOCUMENTS

| | | |
|---|---|---|
| 5,007,420 A | 4/1991 | Bird |
| 5,735,799 A | 4/1998 | Baba |

(Continued)

FOREIGN PATENT DOCUMENTS

| | | | |
|---|---|---|---|
| DE | 102011122905 B3 | 5/2015 | |
| EP | 0872255 A1 | 10/1998 | |

(Continued)

*Primary Examiner* — Jon Eric C Morales
(74) *Attorney, Agent, or Firm* — Lucas & Mercanti, LLP; Klaus P. Stoffel

(57) ABSTRACT

A display for outputting information contents of at least one parameter, adjustment value or measurement value of medical devices within at least one display region, wherein the at least one display region is in the form of a tachometer-like display.

15 Claims, 3 Drawing Sheets

(51) Int. Cl.
   *G16H 40/63* (2018.01)
   *G06T 11/00* (2006.01)
   *G06T 11/20* (2006.01)

(52) U.S. Cl.
   CPC ........... *G06T 11/206* (2013.01); *G16H 40/63* (2018.01); *A61M 2205/054* (2013.01); *A61M 2205/3303* (2013.01); *A61M 2205/505* (2013.01); *A61M 2205/584* (2013.01); *A61N 1/3925* (2013.01)

(58) Field of Classification Search
   CPC .................. A61B 5/748; A61N 1/3993; A61M 2205/502; A61M 2205/505; A61M 16/0057; A61M 16/0063; A61M 2205/6081; A61M 2205/6063; A61M 2205/60
   See application file for complete search history.

(56) References Cited

U.S. PATENT DOCUMENTS

| | | | |
|---|---|---|---|
| 8,016,765 | B2 | 9/2011 | Ramsey |
| 2009/0141593 | A1 | 6/2009 | Taha |
| 2013/0314522 | A1 | 11/2013 | Ravid |
| 2015/0105687 | A1 | 4/2015 | Abreu |
| 2016/0051780 | A1* | 2/2016 | Sherman ............ A61M 16/024 128/204.21 |

FOREIGN PATENT DOCUMENTS

| | | |
|---|---|---|
| EP | 3101882 A2 | 12/2016 |
| WO | 02058619 A2 | 8/2002 |
| WO | 2016018448 A1 | 2/2016 |
| WO | 2017047595 A1 | 3/2017 |

* cited by examiner

DISPLAY FOR OUTPUTTING INFORMATION CONTENTS OF MEDICAL DEVICES

CROSS-REFERENCE TO RELATED APPLICATIONS

The present application is a 371 of International application PCT/DE2018/000040, filed Feb. 16, 2018, which claims priority of DE 10 2017 004 140.7, filed Apr. 27, 2017, and DE 10 2017 007 625.1, filed Aug. 9, 2017, the priority of these applications is hereby claimed and these applications are incorporated herein by reference.

BACKGROUND OF THE INVENTION

The invention relates to a display for outputting information content of at least one parameter, adjustment value or measurement value of medical devices within at least one display region.

For some time now, various equipment and devices have been available to medical technology for the support, maintenance or improvement of different biological functions of human beings and, more generally, mammals and other living creatures. Devices with resuscitation functions are also available for particularly vital biological functions or processes. Biological functions or processes in this context can be, for example, inhalation and exhalation or heart function.

Medical devices for supporting, maintaining or improving inhalation and exhalation can be implemented as ventilators and emergency ventilators, for example. Another well-known device type are dialysis machines for performing blood purification tasks. In the resuscitation of cardiac functions, in particular, defibrillators are used.

Before, during and possibly even after the use of equipment or devices for supporting, maintaining or improving different biological functions a plurality of parameters, adjustment values, measurement values, in particular of a physical nature, are required and/or measured and/or collected or processed. The same applies to their output.

The output of measured values is of particular importance. This is particularly true in the case of the proper, correct and targeted use of such devices by operating personnel, physicians, or in the interaction of multiple devices. For this reason, particularly in ventilators and defibrillators, a plurality of different, preferably physical measurements and/or functional parameters are determined, measured or recorded.

Depending on the type and information content of the parameters, adjustment values or measurement values and/or their manifestation in digital or analog form, it is necessary to provide a suitable representation, with prior processing if necessary.

To implement such outputs, analog or digital displays, such as display screens or special display devices are often used, which display single and/or series of measurement values, parameter values, adjustment values and other physical values. The same applies to the combination of multiple values or families of values, which are also displayed in two- or three-dimensional displays in the form of value fields. Also known in this context are graphical outputs on displays in the form of diagrams, bar charts or graphs.

In particular, in devices with resuscitation and/or respiration functions for particularly vital biological functions or processes, it is important to patient survival that information contents of parameters, adjustment values or measurement values and/or their nature are displayed quickly, unambiguously and with absolute reliability, even in the presence of interference and are presented in such a way that operating personnel can absorb the information content correctly and with certainty.

In known output forms and devices the information contents of the parameters, adjustment values or measurement values and/or their nature are not always reliably readable or understandable. A plurality of sources of error can occur either additively or alternatively: visual misinterpretation, optical confusion of multiple values presented at once, too slow updating on the monitor or display, unsuitable display format of digital or analog values or value sequences, etc.

SUMMARY OF THE INVENTION

It is the object of the invention to at least reduce the above disadvantages in the output of the information contents of parameters, adjustment values or measurement values and/or their nature. In particular, in the specific situation of resuscitation using defibrillators in the context of a ventilation, the object is to visualize the most important parameters for the user such that they can be read quickly, wherein the accuracy becomes less important and facilitates the observance of relevant limits. A further object is to provide an easy-to-read display for resuscitation devices or ventilation devices, in particular for emergency ventilation devices.

The solution according to the invention provides a display in, for or interacting with at least one piece of equipment or device, consisting of, for example, a defibrillator and/or a ventilation unit and/or a combination device and/or monitor, which has a measuring device for discrete, continuous and/or one or more periodically occurring signals with information content with regard to parameters, adjustment values or measurement values and/or their characteristics. It is provided that information contents and/or physical quantities are output as single values in discrete form, continuously, alternately and/or intermittently. Measurement values and other information content to be displayed may originate partially or completely from another device and be transmitted singly, periodically or continuously to the displaying device.

The signals, information content and/or operating instructions for operating personnel are output, for example, as at least one main feature on a display in the form of a tachometer-like representation. In addition, colors are used to identify whether the limits for the displayed parameter are being observed. In addition, the value can be displayed numerically. Optionally, one or more prominent values, a curve or trend representations can be output above or below the tachometer-like display, for example to display processes that change more slowly. In addition, alarms and other measurement values and status data can be presented.

In particular, the tachometer-like display can show the trigger frequency of a ventilator device, in the ventilator mode of which the trigger signal can occur. The permitted limit values to be displayed in this case, for example, are the recommendations of the ERC (European Resuscitation Council VZW) of 100-120/min. The curve can be a respiratory flow curve or an ETCO2 trend curve.

The teaching according to the invention recognizes that the at least partial presentation of information contents of parameters, adjustment values or measurement values and/or their characteristics in a discrete and/or continuous, alternating, asymptotic way by at least one tachometer-like display provides considerable advantages and, in particular, at least partially reduces the disadvantages of known displays. The tachometer-like display realizes, for example, an operating principle of pointer instruments with a rotational pointer, such as are used in analog speedometers in the form of tachometers in vehicles. Such a display is easy and quick to read, even in emergency situations. In particular, it is envisaged to design the display region in different colors. For example, a region with permitted values is shown in green, whereas critical values are shown in red.

In accordance with a further particularly preferred embodiment, the device is used in devices for supporting a cardiac massage. Such a device is used in resuscitation and often combines the ventilation and the resuscitation functions. Firstly, a ventilation and/or supply of oxygen is carried out. In addition, the assistant is provided with a rhythm for performing the cardiac massage. The display can be used both to display the rhythm as well as the intensity of the necessary pressure on the chest. In resuscitations of this kind, the necessary compressions are within a range of 100 to 120 compressions per minute.

BRIEF DESCRIPTION OF THE DRAWING

The drawings illustrate exemplary embodiments of the invention. Shown are.

DETAILED DESCRIPTION OF THE INVENTION

Figure 1:
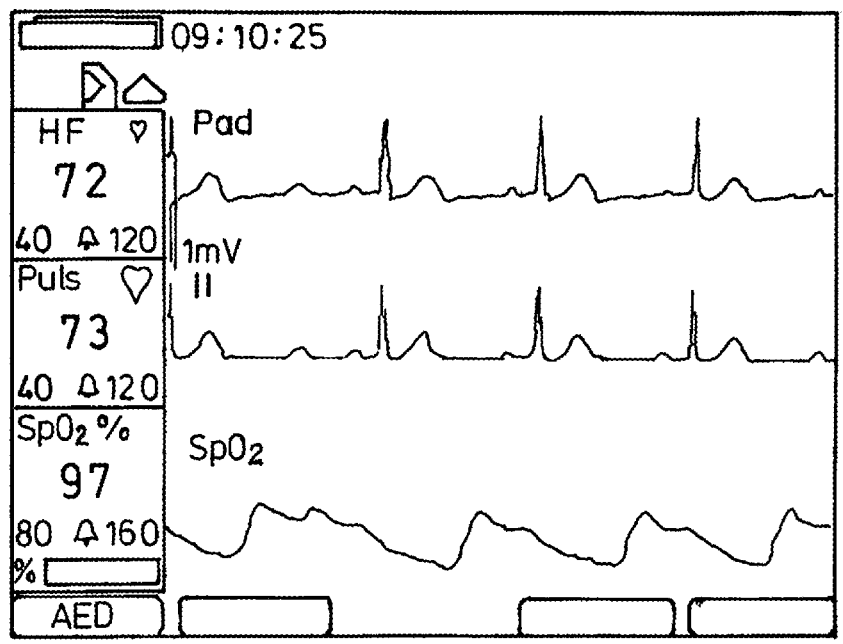
FIG. 1 an example of two display views of a selected example from the prior art, FIG. 2 a first exemplary embodiment of the display (100) according to the invention with information content regarding parameters, adjustment values or measurement values and/or their characteristics in discrete and/or continuous, alternating, and asymptotic form and FIG. 3 an exemplary interaction of the various pieces of equipment and/or devices in the resuscitation of a patient.
Figure 1:
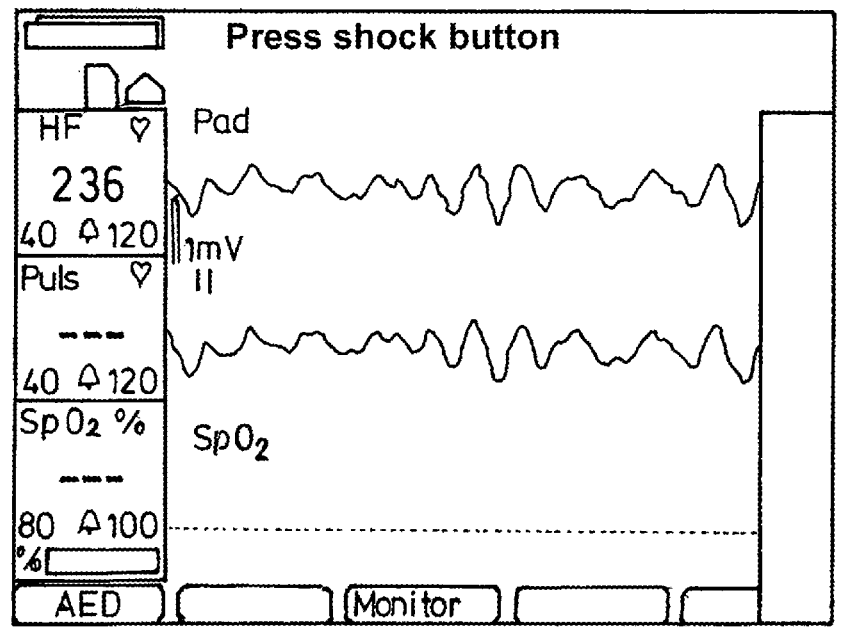

FIG. 1 shows two examples of display screens, each comprising a plurality of measurement panels for displaying various measurements in the form of numerical values and graphs.

Figure 2:
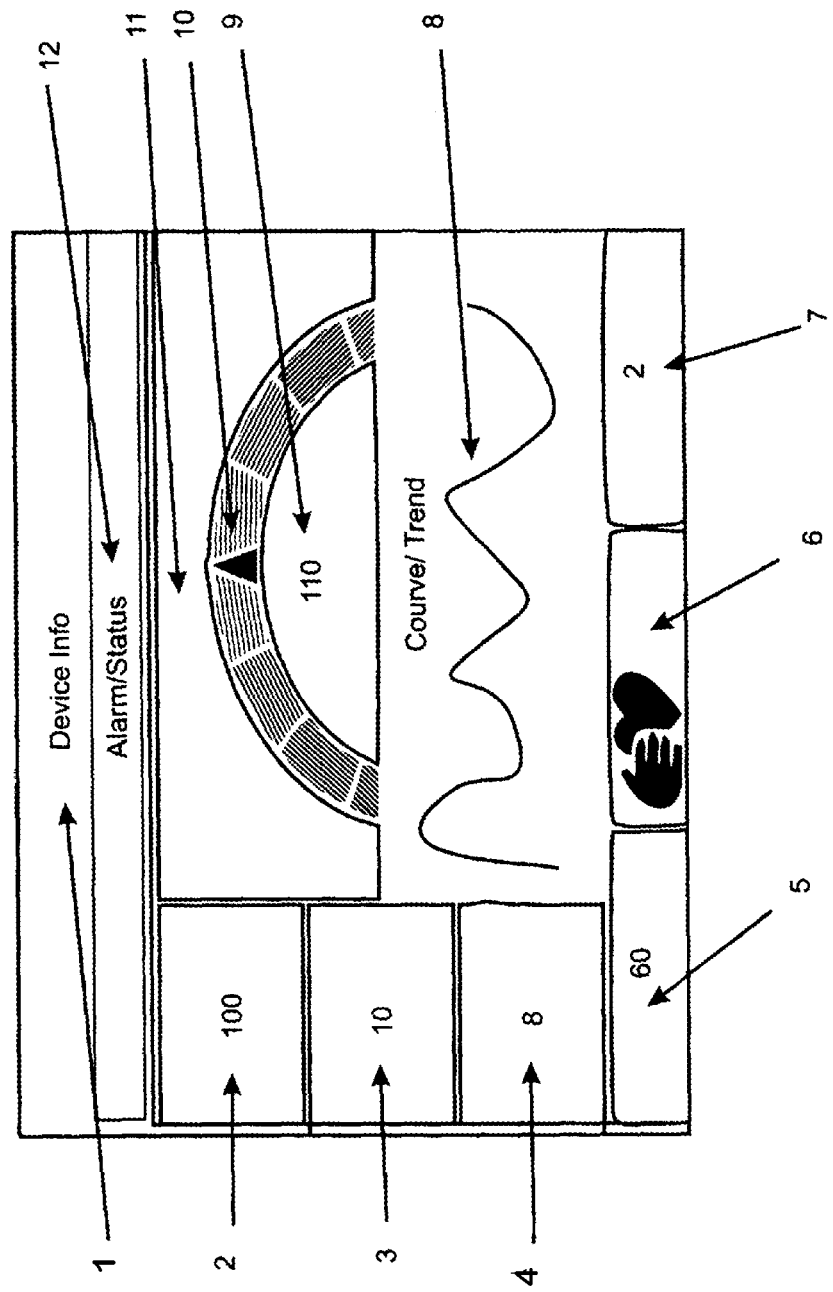

In FIG. 2, the display (100) according to the invention is shown in a first possible design. In addition to the optional display components (1) to (8) and (12) at least one display region (11) is designed in the manner of a tachometer. The tachometer-like display region (11) is formed by a needle (10), which is contained in a variable position relative to an array of values or value ranges, and with its instantaneous position indicates the information content of the value that is present. The value to be displayed in particular is in measurement value (9), which in addition to the displayed information of the needle (10) can be optionally displayed in a numerical form, for example, and in a visually perceptible form.

The motion kinematics of the needle (10) or the tachometer-like display region (11) with a panel containing values, measurement values or measurement value ranges can be implemented in a rotary manner by analogy to round instruments of classic tachometers so as to realize the relative position changes with respect to each other. Also provided are different types of movement paths, for example, by free-form tracks, linear movements, elliptical kinematics or trajectories along stochastically random paths. It is also conceivable for the needle (10) to be stationary and the panel containing values, measurement values or measurement value ranges to follow one of the motion kinematics mentioned. The same applies to combined motion kinematics realized by the needle (10) and the display region (11).

The example shown in FIG. 2 provides a rotary motion kinematics for the needle (10) with possible instantaneous positions above or within value ranges arranged in a semi-round pattern that the needle (10) sweeps over.

Figure 3:
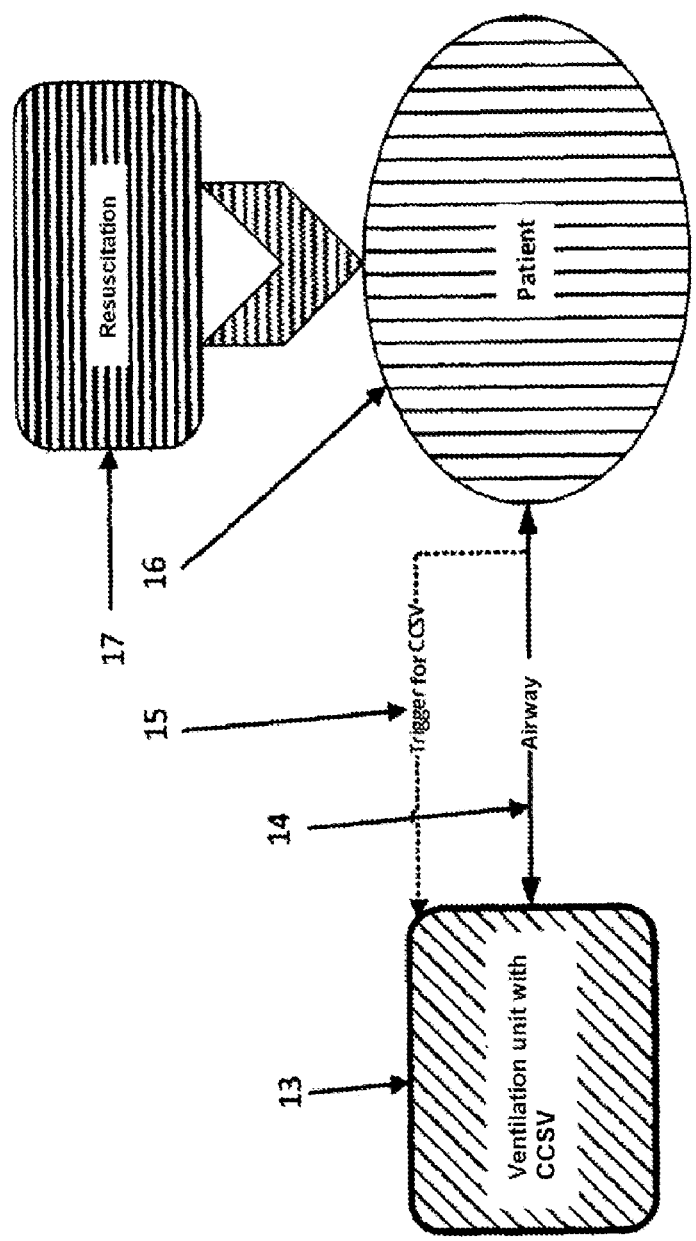

FIG. 3 shows an exemplary interaction of the different pieces of equipment and/or devices in the resuscitation of a patient. The resuscitation or thoracic compression (17) is used to revive a patient (16) and counteracts respiratory and circulatory arrest. The thoracic compression (17) can be optionally combined with a ventilator or emergency ventilator (13) as shown in FIG. 3. To this end, the patient (16) is coupled to the ventilation device or emergency ventilation device (13) by means of a ventilation hose system (14). The ventilation hose system (14) can optionally comprise a means of securing the airway.

According to the invention, the ventilator or emergency ventilator (13) can implement the breathing pattern known as CCSV (chest compression synchronized ventilation). This breathing pattern supports the simultaneous insufflation with each chest compression, preferably with the following ventilation parameters: Tinsp=0.2 s, Pinsp=60 (+−10%) mbar, f=100/min, PEEP=0 mbar, Pmax=65 mbar, FiO2=1.0. A respiration-dependent trigger signal (15) is provided to the ventilator, emergency ventilator (13) and can be, in particular, a measurement value to be displayed within the tachometer-like display region (11) of the display (100).

The invention claimed is:

1. A display for outputting information contents of at least one parameter, adjustment value or measurement value of a medical device the display comprising at least one display region formed as a tachometer-like display, wherein the tachometer-like display includes at least one needle and at least one panel containing values, measurement values or measurement value ranges, wherein the tachometer-like display is operatively configured to implement an output of information contents of at least one parameter, adjustment value or measurement value of medical devices by a change of position of the at least one needle relative to the panel containing values, measurement values or measurement value ranges, wherein the panel containing values, measurement values or measurement value ranges is arranged in a semi-circular manner within the display region.

2. The display according to claim 1, wherein the change in position of the at least one needle relative to the panel containing values, measurement values or measurement value ranges takes place due to a movement of the needle and/or of the panel.

3. The display according to claim 2, wherein motion kinematics for the relative position change follow a rotary trajectory.

4. The display according to claim 1, wherein the output of information content of at least one parameter, adjustment value or measurement value of medical devices is realized additively by the display of the numerical value.

5. The display according to claim 1, wherein the display is a display or monitor or bistable display or e-paper display or a touch screen.

6. The display according to claim 1, wherein the medical device is a ventilator, an emergency ventilator and/or a defibrillator.

7. The display according to claim 1, wherein the at least one parameter, adjustment value or measurement value is displayed in analog and/or digital form.

8. The display according to claim 1, wherein information content of the at least one parameter adjustment value or measurement value is displayed as a discrete or continuous or alternating or intermittent biological or physical quantity.

9. The display according to claim 1, wherein the at least one parameter is an alarm signal and/or an action instruction and/or a setpoint specification and/or at least one ventilation parameter.

10. The display according to claim 9, wherein the at least one ventilation parameter is Tinsp=0.2 s and/or Pinsp=60 (+−10%) mbar and/or f=100/min and/or PEEP=0 mbar and/or Pmax=65 mbar and/or FiO2=1.0 and/or Pinsp=40 DAzw.

11. The display according to claim 1, wherein the at least one adjustment value is a trigger signal and/or a limit value of a biological function to be measured.

12. The display according to claim 1, wherein the at least one measurement value is a trigger frequency and/or a setpoint or actual compression rhythm and/or a pulse frequency.

13. A medical device having a display according to claim 1.

14. A display for outputting information contents of at least one parameter, adjustment value or measurement value of a medical device the display comprising at least one display region formed as a tachometer-like display, wherein an information content of the at least one parameter, adjustment value or measurement value is displayed in different colors.

15. The display according to claim 14, wherein the coloring of the at least one parameter, adjustment value or measurement value changes to a red color if the information content is a limit violation and/or an alarm.

* * * * *